(12) United States Patent
Gleeson et al.

(10) Patent No.: US 8,821,502 B2
(45) Date of Patent: Sep. 2, 2014

(54) INSTRUMENT AND METHOD FOR SPINAL COMPRESSION AND DISTRACTION

(75) Inventors: Garrett Gleeson, Carlsbad, CA (US); Clark Hutton, Oceanside, CA (US); Nathan Meyer, Vista, CA (US); Anand Parikh, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 206 days.

(21) Appl. No.: 13/409,711

(22) Filed: Mar. 1, 2012

(65) Prior Publication Data

US 2012/0239096 A1    Sep. 20, 2012

Related U.S. Application Data

(63) Continuation-in-part of application No. 12/462,974, filed on Aug. 11, 2009, now Pat. No. 8,394,109, which is a continuation-in-part of application No. 12/290,035, filed on Oct. 23, 2008, now Pat. No. 8,469,960.

(60) Provisional application No. 61/000,263, filed on Oct. 23, 2007, provisional application No. 61/132,974, filed on Jun. 23, 2008.

(51) Int. Cl.
*A61B 17/58* (2006.01)
*A61B 17/60* (2006.01)
*A61F 2/00* (2006.01)
*A61B 17/70* (2006.01)

(52) U.S. Cl.
CPC .................................... *A61B 17/708* (2013.01)
USPC ............................................ 606/90; 606/105

(58) Field of Classification Search
CPC ............ A61B 17/6425; A61B 17/708; A61B 17/7079; A61B 17/7076; A61B 17/7077
USPC .................................................... 606/90, 105
See application file for complete search history.

(56) References Cited

U.S. PATENT DOCUMENTS

| | | | |
|---|---|---|---|
| 8,435,269 B2 * | 5/2013 | Woolley et al. | 606/279 |
| 2005/0245928 A1 * | 11/2005 | Colleran et al. | 606/61 |
| 2008/0077155 A1 * | 3/2008 | Diederich et al. | 606/105 |
| 2009/0076515 A1 * | 3/2009 | Lamartina et al. | 606/90 |
| 2013/0110184 A1 * | 5/2013 | Wing et al. | 606/86 A |

* cited by examiner

*Primary Examiner* — David Bates
(74) *Attorney, Agent, or Firm* — Michael J. Loi

(57) ABSTRACT

An instrument for multilevel compression and distraction of vertebrae in a spinal column includes a first arm, a second arm, a third arm, a linking member, and a coupler. The first arm includes a distal end with a first aperture for receiving a first screw extender that attaches to a first vertebra. The second arm includes a distal end with a second aperture for receiving a second screw extender that attaches to a second vertebra. The third arm includes a distal end with a third aperture for receiving a third screw extender that attaches to a third vertebra. The linking member pivotally links proximal ends of the first, second, and third arms. The coupler positions the distal ends of the first arm and the second arm relative to the third arm to compress and distract the first vertebra and the second vertebra relative to the third vertebra.

18 Claims, 16 Drawing Sheets

INSTRUMENT AND METHOD FOR SPINAL COMPRESSION AND DISTRACTION

CROSS-REFERENCE TO RELATED APPLICATIONS

The present application is a continuation-in-part application of U.S. patent application Ser. No. 12/462,974 to Hutton et al., filed Aug. 11, 2009 now U.S. Pat. No. 8,394,109, and entitled "Systems and Methods for Spinal Fixation", which is a continuation-in-part application of U.S. patent application Ser. No. 12/290,035 to Hutton et al., filed Oct. 23, 2008 now U.S. Pat. No. 8,469,960, and entitled "Systems and Methods for Spinal Fixation", which claims priority to U.S. Provisional Patent Application No. 61/000,263 to Hutton et al., filed Oct. 23, 2007, and entitled "Percutaneous Wire System" and to U.S. Provisional Patent Application No. 61/132,974 to Hutton et al., filed Jun. 23, 2008, and entitled "Method And Device For Percutaneous Spinal Fixation". The present application incorporates disclosures of these applications herein by reference in their entireties.

FIELD

The present invention relates to surgical methods and devices for spinal surgery, and in particular to an instrument and method for applying compression and/or distraction forces to the spine.

BACKGROUND

In many surgical spinal procedures, such as the correction of scoliosis, nerve root decompression, interbody fusion, tumor removal, repair of kyphosis, and treatment of other spinal defects or trauma, it is desirable or necessary to supply forces by compression and/or distraction to vertebrae in the defective region. In some cases, the defective region includes lordotic curvature. The defective region may also include multiple levels of vertebrae. In some cases, one of the levels of the spine must be skipped during the compression and distraction procedures.

Typically, pedicle screws are inserted into the vertebrae of the defective region and spinal rods are used to rigidly fix the vertebrae relative to one another. Screw extenders may be used to assist with insertion of the spinal rods and to transmit the compressive and distracting forces of a compressor/distractor instrument. While there are instruments that exist for applying these forces to the spine, there remains a need for instruments and methods that improve surgeon efficiency and provide the surgeon additional options in the application of such forces. The present invention is directed toward meeting these needs and others including providing options that permit skipping levels of the spine during compression and distraction procedures.

SUMMARY

An instrument for multilevel compression and distraction of vertebrae in a spinal column includes a first arm, a second arm, a third arm, a linking member, and a coupler. The first arm includes a distal end with a first aperture for receiving a first screw extender that attaches to a first vertebra. The second arm includes a distal end with a second aperture for receiving a second screw extender that attaches to a second vertebra. The third arm includes a distal end with a third aperture for receiving a third screw extender that attaches to a third vertebra. The linking member pivotally links proximal ends of the first, second, and third arms. The coupler positions the distal ends of the first arm and the second arm relative to the third arm to compress and distract the first vertebra and the second vertebra relative to the third vertebra.

In other features, the first arm and the second arm are disposed on opposite sides of the third arm. A slot in the distal end of the third arm for receives a wheel on the coupler. Coupler apertures in the distal ends of the first arm and the second arm receive the coupler. Pivot collars that pivot within the coupler apertures and engage threads of the coupler pivotally link the coupler with the first arm and the second arm. Rotating the coupler in a first direction positions the first arm and the second arm away from the third arm. Rotating the coupler in a second direction positions the first arm and the second arm towards the third arm. The first and second apertures include first and second longitudinal axes in a common plane and the third aperture includes a third longitudinal axis that intersects the common plane. The first, second, and third apertures include one or more attachment features for attachment to the screw extenders. Each of the first, second, and third apertures includes one or more tabs extending inwardly for alignment and attachment to the screw extenders.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific examples of the invention. Furthermore, examples of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1A:
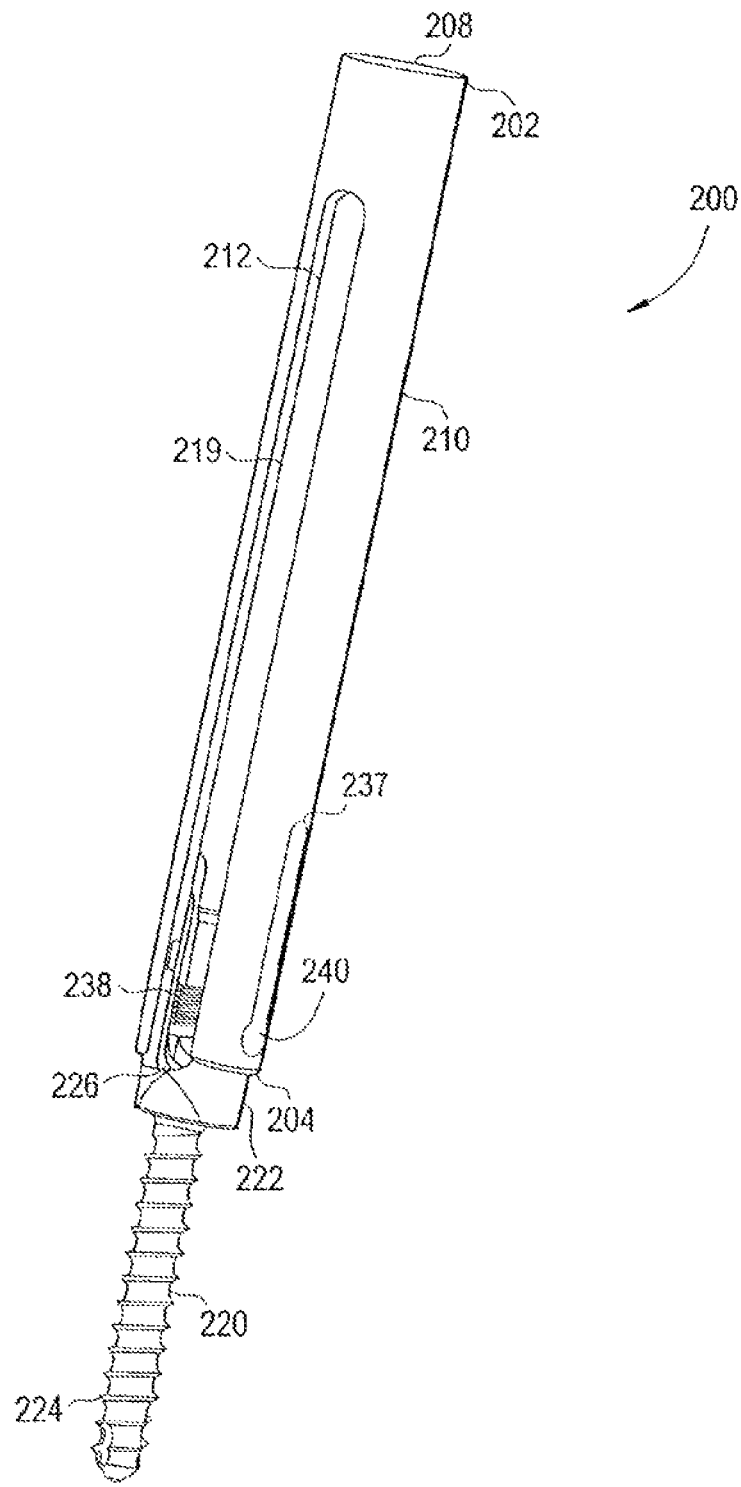
FIGS. 1A and 1B illustrate an exemplary screw extender system according to the principles of the present disclosure.
Figure 1B:
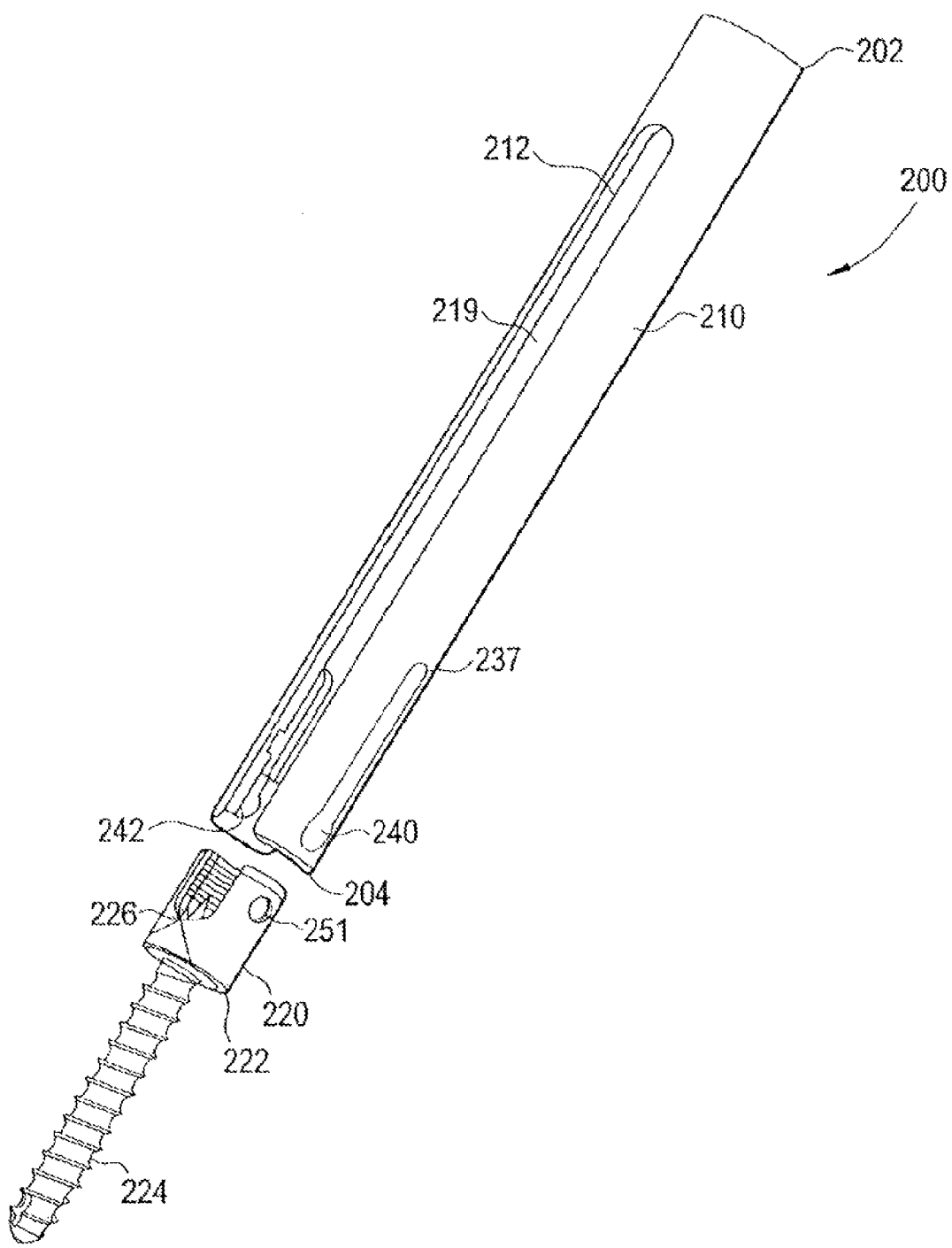

FIGS. 1A and 1B illustrate an exemplary screw extender system 200, according to some embodiments of the present invention. FIG. 1A illustrates a screw extender housing 210 being coupled to a screw 220 and FIG. 1B illustrates the screw extender housing 210 being uncoupled from the screw 220. As shown in FIGS. 1A and 1B, a screw 220 is configured to be coupled to a screw extender housing 210. The screw extender housing 210 is configured to be an elongated tube that includes openings at both of its ends 202 (proximal), 204 (distal) for coupling to the screw 220 at one end 204 and for insertion of surgical instruments at the other end 202. The housing 210 further includes slots or channels 212 that extend along at least a portion of the housing 210 and are further configured to accommodate placements of rod(s). Additionally, the housing 210 further includes indentor portions or screw-locking features 240, which are configured to secure the screw 220 to the screw extender device housing 210. In some embodiments, the housing 210 includes two indentor portions 240 (second portion is not shown in FIG. 1A). The indentor portions 240 are configured to be fixed to the housing 210 at a location 237, which is disposed toward the screw-coupling end 204. In some embodiments, the indentor portions 240 are configured to be welded at a location 237. Once the screw 220 is loaded into the extender device (See, FIG. 1A), the indentor portions 240 are configured to engage the screw 220 using protrusions 242 that are disposed on an interior wall of the indentor portions 240 and are further configured to protrude into the interior of the housing 210. In some embodiments, the indentor portions 240 are configured to be flexible.

The indentor portions 240 are configured to engage an opening 251 in the head of the screw 220, as shown in FIG. 1B. Upon insertion of the screw 220 into the extender device housing 210, the indentor portions 240 are configured to spread apart from the center of the housing 210. In some embodiments, the indentor portions 240 are configured to be spring-like devices that pull apart upon application of external mechanical pressure. Once the screw 220 is inserted into the housing 210, the indentor portions 240 are configured to snap into openings 251 of the screw 220. Upon snapping into openings 251, the indentor portions 240 rigidly secure the screw 220 to the housing 210.

The screw extender housing 210 includes an interior passageway 219 that is configured to be exposed by the channel 212 (either fully or partially stretching along the length of the housing 210). The channel 212 is configured to be aligned with a passageway 226 disposed on the head of the screw 222 so as to create a continuous channel between the between the channel 212 and the passageway 226 for passing of tools, instruments, rods, etc.

Figure 2A:
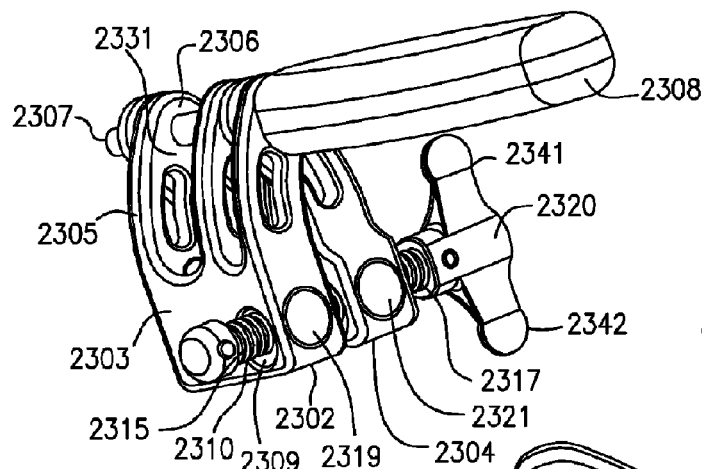
FIGS. 2A-2I illustrate an exemplary compression-distraction tool according to the principles of the present disclosure.
Figure 2B:
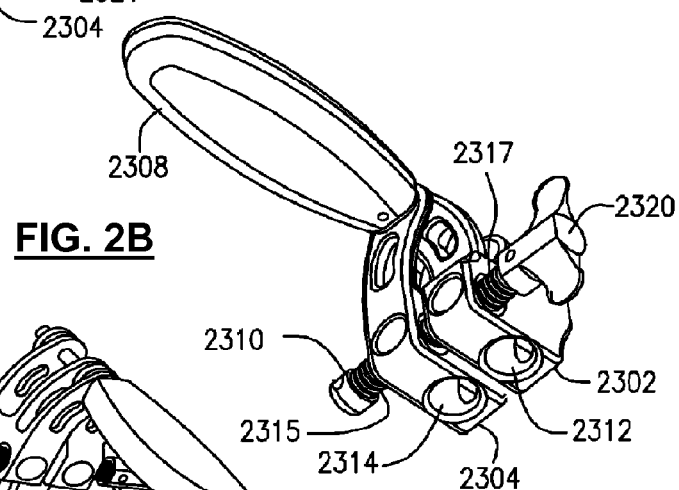
Figure 2C:
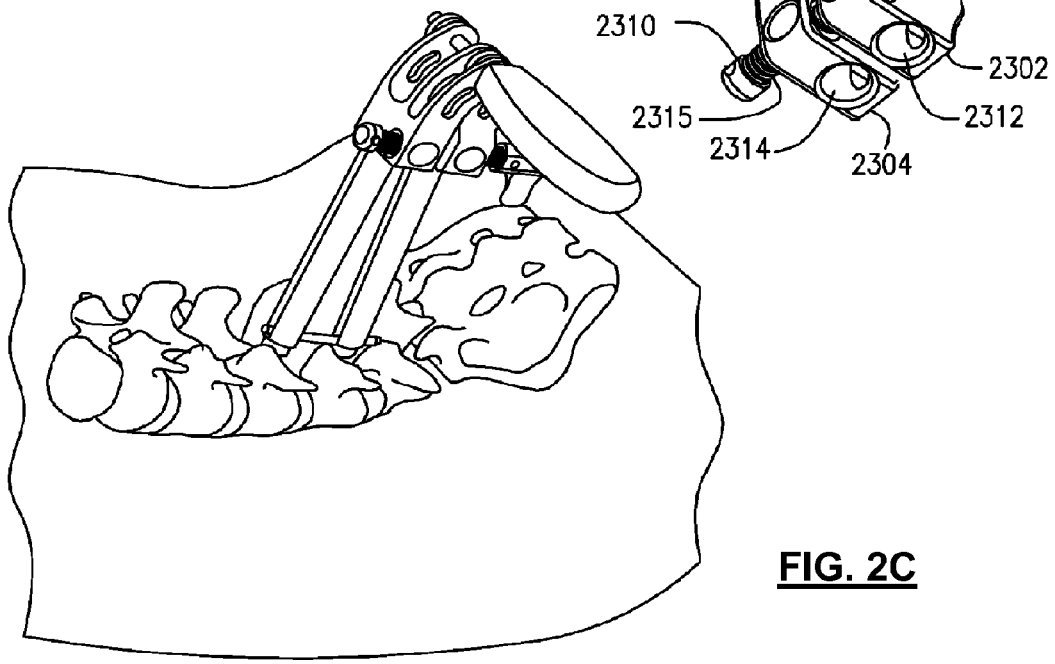
Figure 2D:
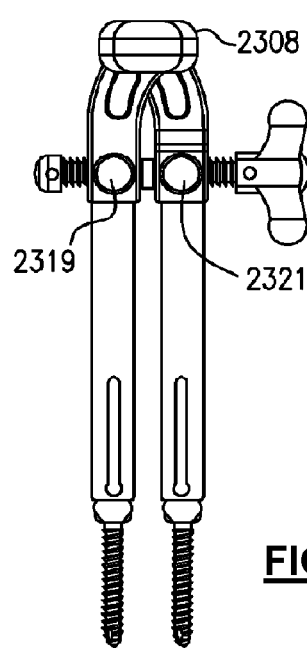
Figure 2E:
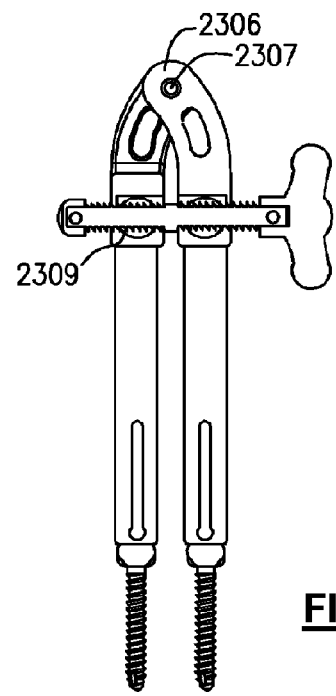
Figure 2F:
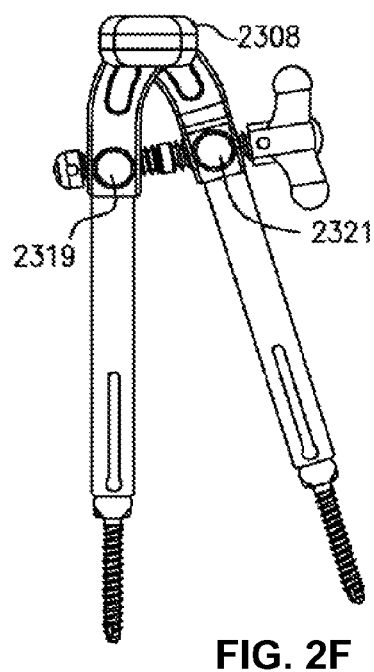
Figure 2G:
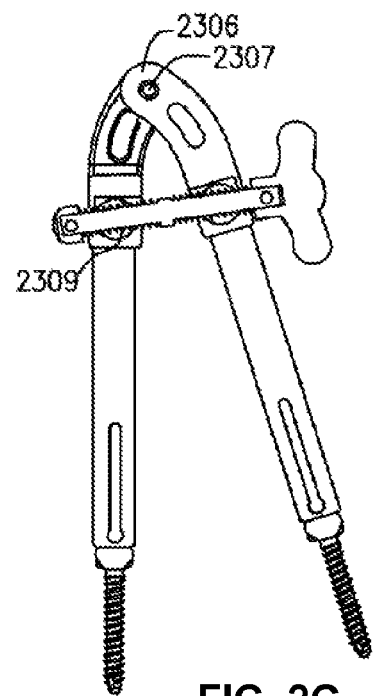
Figures 2H, 2I:
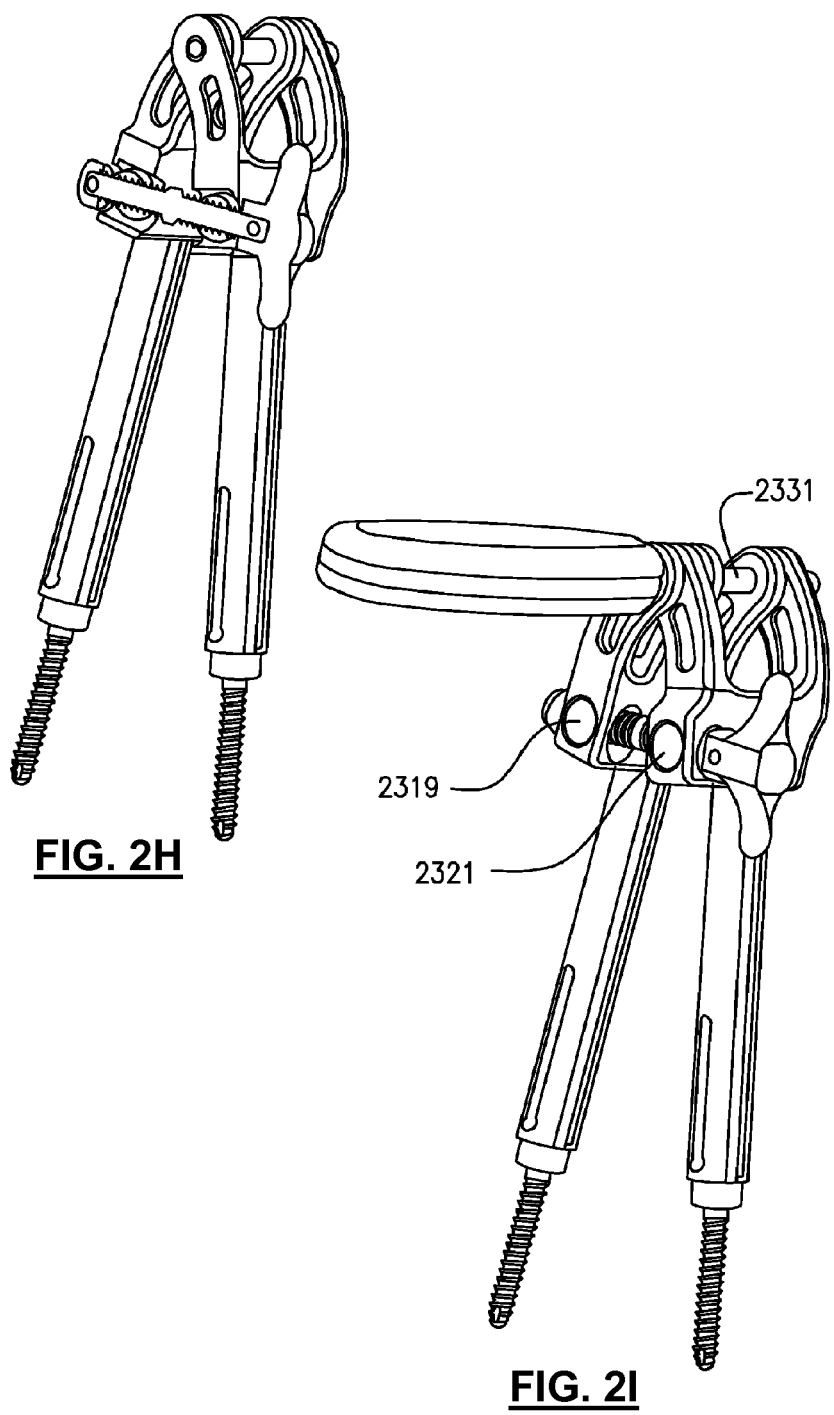

FIGS. 2A-2I illustrate an exemplary compressor-distractor tool 2300, according to some embodiments of the present invention. FIGS. 2A and 2B illustrate perspective views of the tool 2300; FIG. 2C illustrates the tool 2300 being coupled to screw extenders that are attached to respective screws implanted into a vertebrae; FIGS. 2D and 2E illustrate the tool 2300 being in a compressed state (FIG. 2D is a perspective view and FIG. 2E is a cross-sectional view); FIGS. 2F and 2G illustrate the tool 2300 being in a distracted state (FIG. 2F is a perspective view and FIG. 2G is a cross-sectional view); FIGS. 2H and 2I are perspective views of the tool 2300 being attached to screw extenders along with respective screw assemblies.

Referring to FIGS. 2A-2I, the tool 2300 is configured to apply compressive and/or distractive forces to screw extenders and, ultimately, screw assemblies that have been implanted into vertebra and coupled to the screw extenders. In some embodiments, the tool 2300 is placed over top portions of two screw extenders that can be adjacent to one another and then, by turning a handle or a knob, the screw extender assemblies can be compressed together or distracted from each other, as shown in FIG. 2C-2G.

In some embodiments, the tool 2300 includes a first screw extender holding portion 2302 and a second screw extender holding portion 2304, as shown in FIGS. 2A and 2B. Each portion 2302, 2304 can be configured to have a respective base part 2303 coupled to a respective top part 2305. The base part 2303 is configured to be coupled to a screw extender (not shown in FIGS. 2A and 2B). The top part 2305 is configured to protrude away from the base part 2303 and, in some embodiments, can be further configured to have a curvature. The top parts of the portions 2302 and 2304 can be configured to curve toward each other, where portions 2302 and 2304 are pivotally coupled to each other at their respective tops, as shown in FIGS. 2A and 2B.

The portions 2302 and 2304 are pivotally coupled to each other using a pivoted connection 2306. In some embodiments, a removable handle 2308 coupled to a rod 2307 can be inserted through openings at the top of the portions 2302 and 2304 to allow pivoting of the portions 2302, 2304 about the rod 2307.

The base parts 2303 of each portion 2302 and 2304 include respective screw extender openings 2312 and 2314 disposed at the bottom of the respective base parts. The openings 2312 and 2314 are configured to receive upper portions of screw extenders, i.e., tool 2300 is placed on top of the extenders using the openings 2312 and 2314, as shown in FIGS. 23C-23I.

The tool 2300 further includes a multi-threaded screw 2310 that is configured to further connect the portions 2302 and 2304 at their base parts 2303. The screw 2310 is configured to be inserted through openings 2309, where the openings 2309 are configured to be disposed substantially perpendicularly to the openings 2312 and 2314. The screw 2310 is configured to include multi-directional threading 2315 and 2317 that is disposed at opposite ends of the screw. The base parts 2303 of each portion 2302, 2304 include respective threading mechanisms 2319, 2321. The mechanism 2319 is configured to interact with threading 2315 of the screw 2310 and mechanism 2321 is configured to interact with threading 2317 of the screw 2310. The screw 2310 can be further configured to include a handle 2320 for rotating the screw once it is inserted through the openings 2309. Since threading 2315 and 2317 have oppositely disposed threads, rotation of the handle 2320 and the screw 2310 in one direction (e.g., clockwise direction 2341) causes base parts 2303 of portions 2302 and 2304 to come closer to each other (i.e., compression). Similarly, rotation of the handle 2320 and the screw 2310 in an opposite direction (e.g., counterclockwise direction 2342) causes base parts 2303 of portions 2302 and 2304 to spread apart from each other (i.e., distraction). Such movement of the base parts 2303 translates into compression/distraction movement of the screw extender towers inserted into the respective openings 2312 and 2314. Compressed extenders are illustrated in FIGS. 2D and 2E. Distracted extenders are illustrated in FIGS. 2F-2I. Because the screw 2310 rotates at the same angular velocity, equal rotational force is applied to the portions 2302 and 2304 that allows the portions to translate along the length of the screw 2310 equally in their respective directions (which depends on compression or distraction).

In some embodiments, the fulcrum handle 2308 can be configured to be removable and can be further configured to accommodate right-handed or left-handed usage. This is advantageous in the event that the portions 2302 and 2304 may need to be separated.

As shown in FIG. 2A, the respective top parts 2305 of the portions 2302 and 2304 can be configured to include openings 2331 that allow access to the screw extender towers that are inserted into the respective openings 2312 and 2314. The surgeon (or other medical professional) can insert instruments or any other tools through the top parts 2305 and respective openings 2331 of the tool 2300 and into the screw extender towers. The openings 2331 can be also configured to provide a visual indicator of the placement of the screws through the screw extender towers/housings.

As can be understood by one skilled in the art, the tool 2300 can be configured to compress/distract at least two screw extender towers.

Figure 3A:
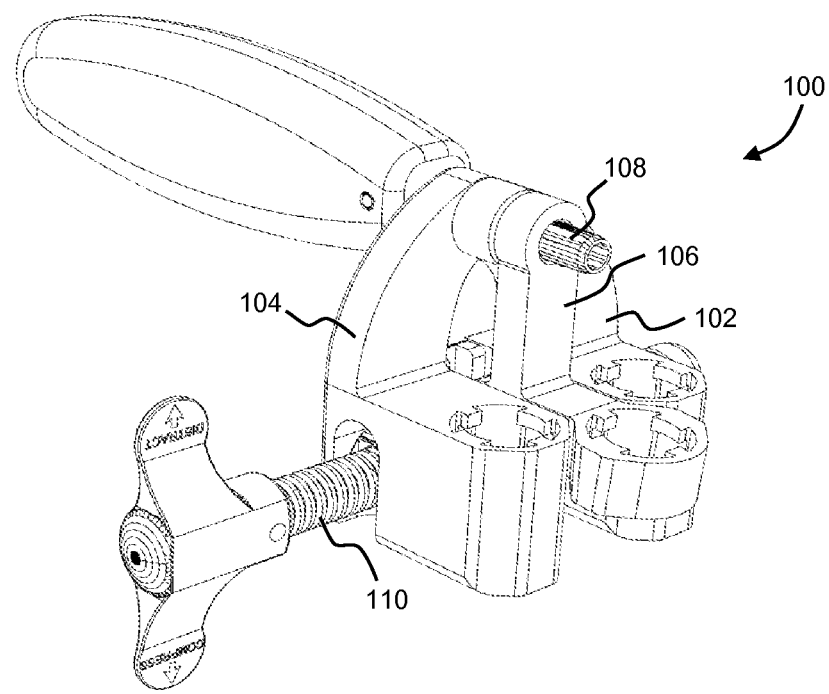
FIGS. 3A and 3B are front and rear perspective views of an instrument for multilevel spinal compression and distraction according to the principles of the present disclosure.
Figure 3B:
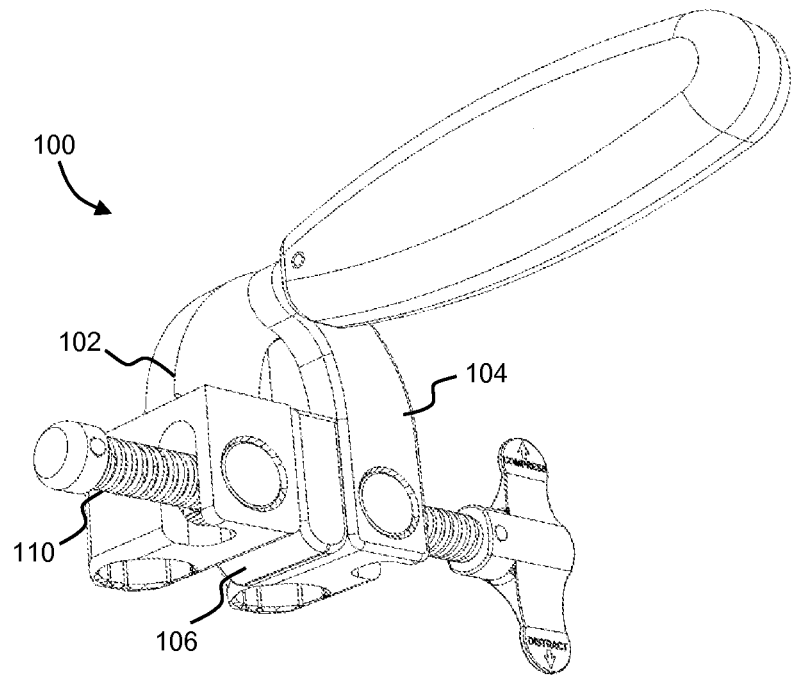
Figure 12A:
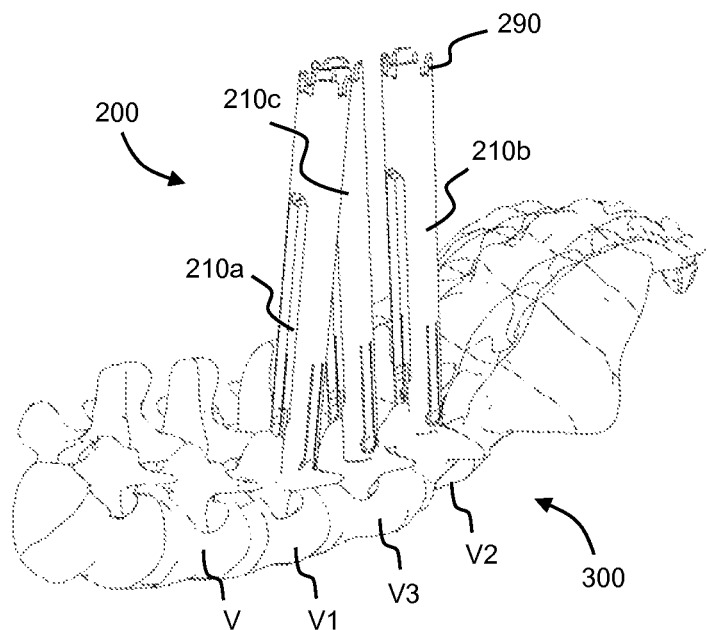
FIGS. 12A and 12B are perspective views of a portion of a spinal column with attached screw extenders and the instrument according to the principles of the present disclosure.
Figure 12B:
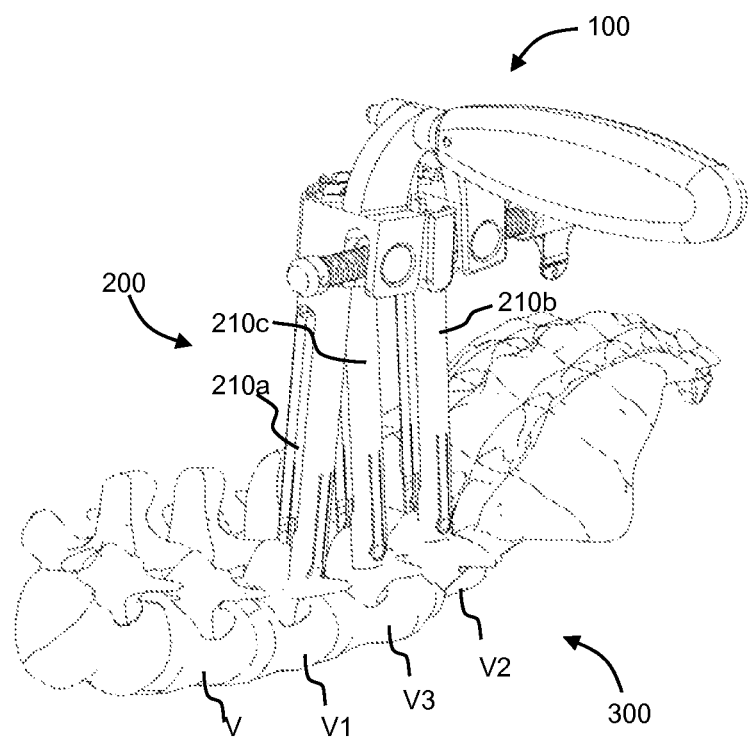

FIGS. 3A and 3B illustrate another exemplary compressor-distractor instrument 100, according to the principles of the present invention. The instrument 100 may be used, for example, for multilevel compression and distraction of vertebrae V of a spinal column 300 using the screw extender system 200 as illustrated in FIGS. 12A and 12B. The instrument 100 includes screw extender holding portions such as a first arm 102, a second arm 104, and a third arm 106. Each of the arms 102-106 is configured for attachment to one of the screw extenders 210 of the system 200 as described herein. A linking member 108 passes through proximal ends of the arms 102-106 and pivotally links the proximal ends of the first arm 102, second arm 104, and third arm 106. An adjustable coupler 110 passes through distal ends of the arms 102-106 and positions the distal ends of the first arm 102 and second arm 104 relative to the third arm 106 to compress and distract a first vertebra V1 and a second vertebra V2 relative to a third vertebra V3 as shown in FIG. 12B. The instrument 100 may be configured to include the third arm 106 for multilevel compression/distraction procedures or to exclude the third arm 106 for single level compression/distraction procedures as described above. Further, the instrument 100 may be easily disassembled for cleaning and sterilization purposes as shown in the exploded view of FIG. 4.

Figure 4:
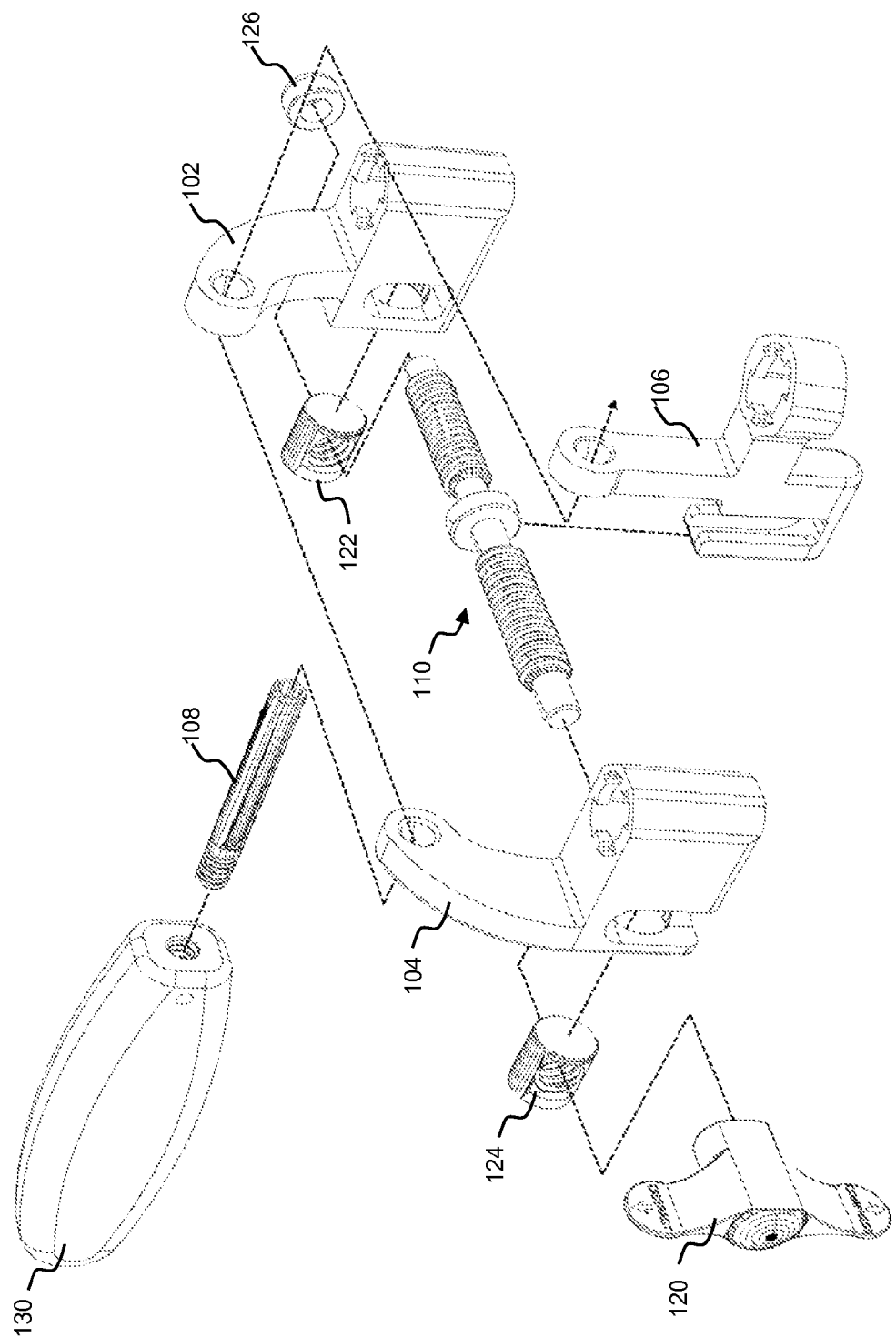
FIG. 4 is an exploded perspective view of the instrument according to the principles of the present disclosure.
Figure 5A:
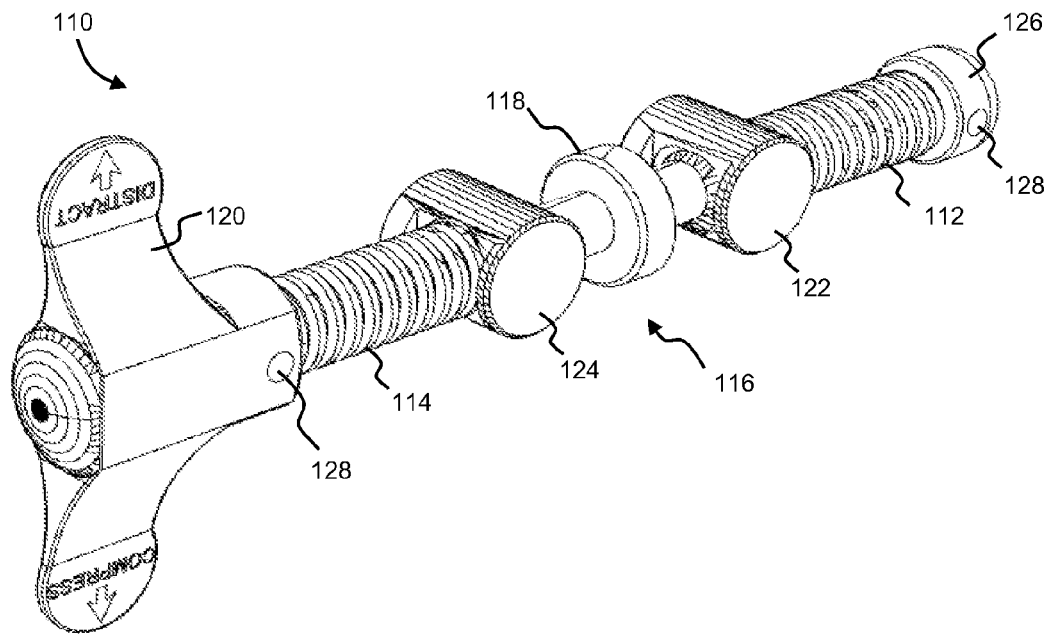
FIGS. 5A and 5B are front and rear perspective views of a coupler of the instrument according to the principles of the present disclosure.
Figure 5B:
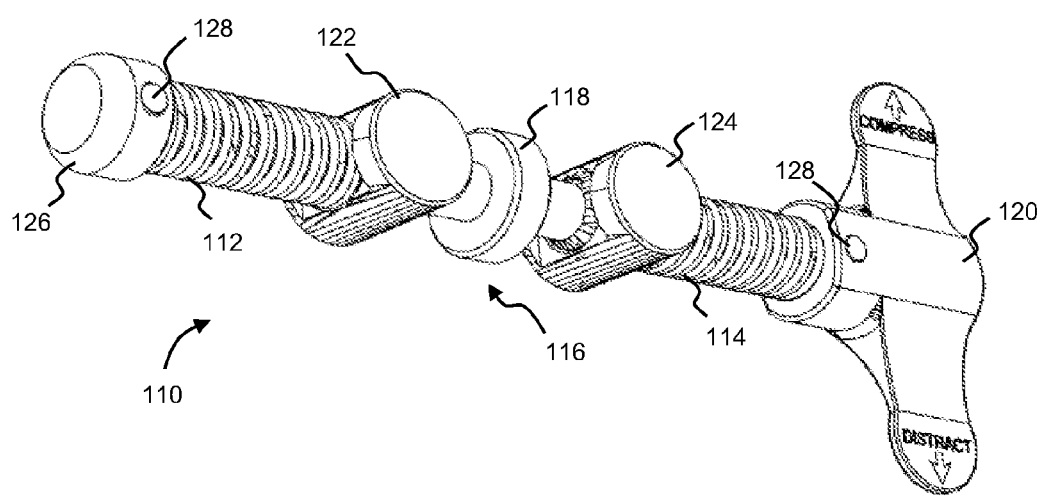

FIGS. 4, 5A, and 5B illustrate additional features of the instrument 100 for positioning of the first arm 102 and second arm 104 relative to the third arm 106 using the coupler 110. The coupler 110 includes one or more threaded portions for engagement with various ones of the arms 102-106. For example, the coupler 110 includes a first threaded portion 112 and a second threaded portion 114. The first threaded portion 112 may position the first arm 102 and the second threaded portion 114 may position the second arm 104. The coupler 110 may further include a retaining portion 116 between the threaded portions 112, 114. The retaining portion 116 may rotate freely within the third arm 106 as the coupler 110 positions the first arm 102 and the second arm 104. For example, the retaining portion 116 may include a retention wheel 118 that rotates within the distal end of the third arm 106. The retention wheel 118 may also slide relative to the distal end of the third arm 106 as described below.

The coupler 110 may further include an actuator 120 on one end of the coupler 110 that may provide additional leverage to rotate the coupler 110. A first pivot nut 122 may pivot within the distal end of the first arm 102. A second pivot nut 124 may pivot within the distal end of the second arm 104. Each of the pivot nuts 122 and 124 may include a substantially cylindrical shape with a threaded aperture 125 passing through the cylinder wall. The interior threads provide engagement with the threaded portions 112 and 114 of the coupler 110. A cap 126 on a second end of the coupler 110 may prevent over extension of the first arm 102 and second arm 104. Various lock pins 128 may be used to removably affix any of the retention wheel 118, actuator 120, and cap 126 to the coupler 110. Similarly, one of the lock pins 128 may be used to removably affix a handle 130 to the linking member 108.

Figure 6A:
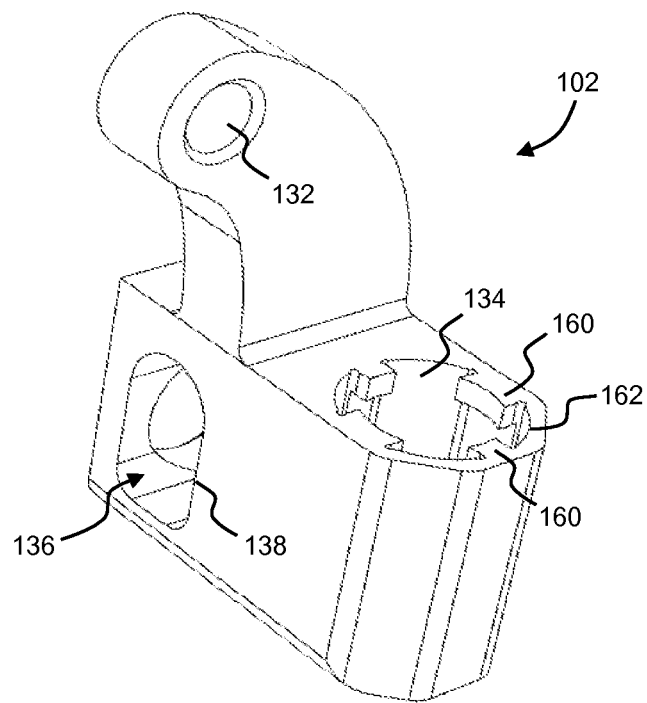
FIGS. 6A and 6B are front and rear perspective views of a first arm of the instrument according to the principles of the present disclosure.
Figure 6B:
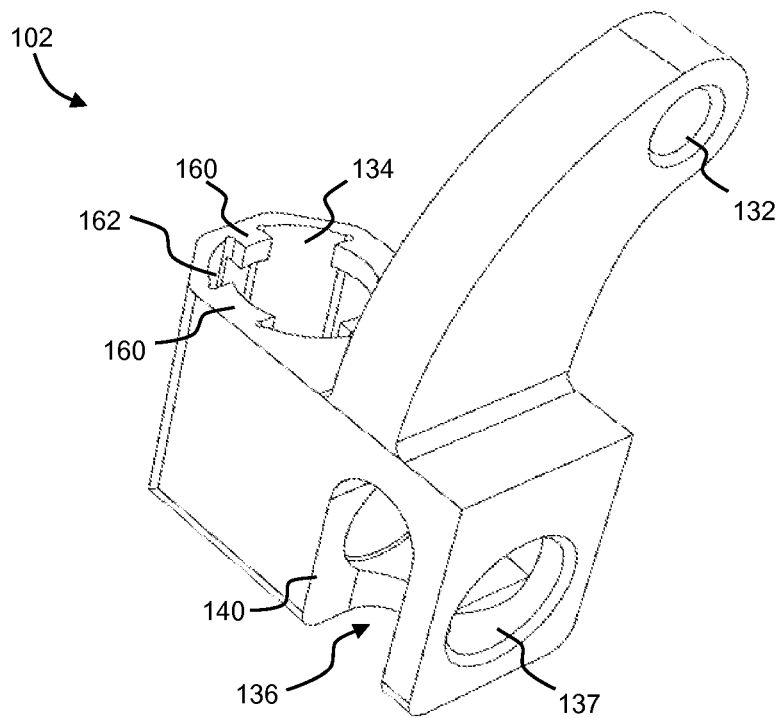

Referring now to FIGS. 4, 6A, and 6B, the first arm 102 includes an aperture 132 at the proximal end for receiving the linking member 108 and enabling the first arm 102 to pivot about the linking member 108. A front portion of the distal end includes a first screw extender (SE) receiver 134 for receiving a first one of the screw extenders 210 as shown in FIGS. 11A-12B. A rear portion of the distal end includes a first cavity 136 that receives the first pivot nut 122. The first cavity 136 may include a substantially cylindrical portion 137 that receives the first pivot nut 122. The cylindrical portion 137 may extend parallel to the linking member 108 and perpendicular to the coupler 110 of the assembled instrument 100. The first cavity 136 may communicate with an inner opening 138 on an inner surface of the distal end and an outer opening 140 on an outer surface of the distal end to allow the coupler 110 to pass through and rotate through a predetermined angle.

Figure 7A:
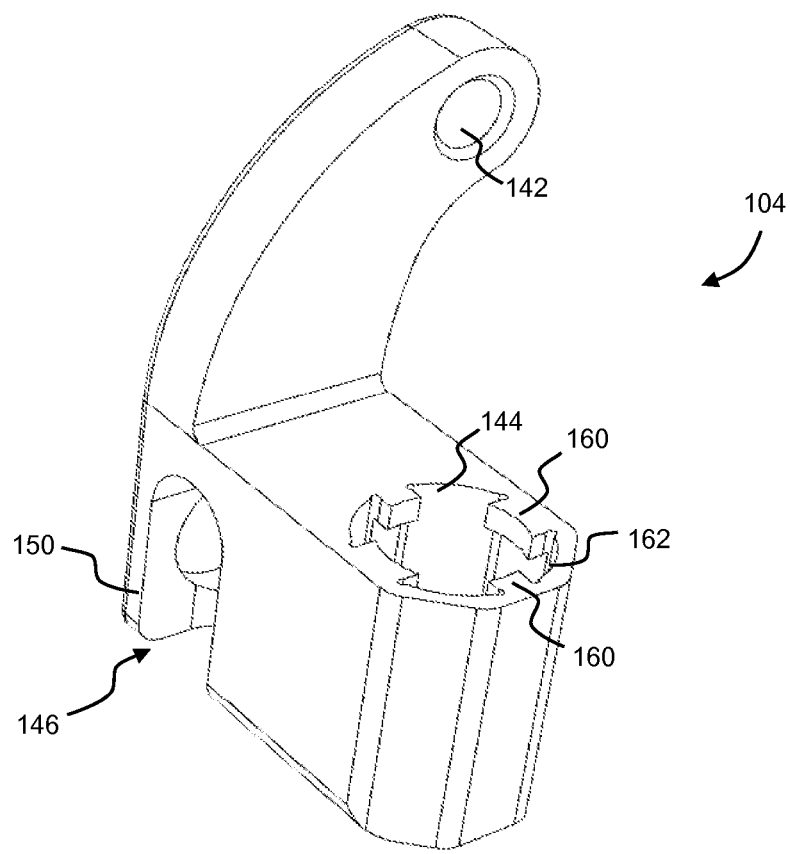
FIGS. 7A and 7B are front and rear perspective views of a second arm of the instrument according to the principles of the present disclosure.
Figure 7B:
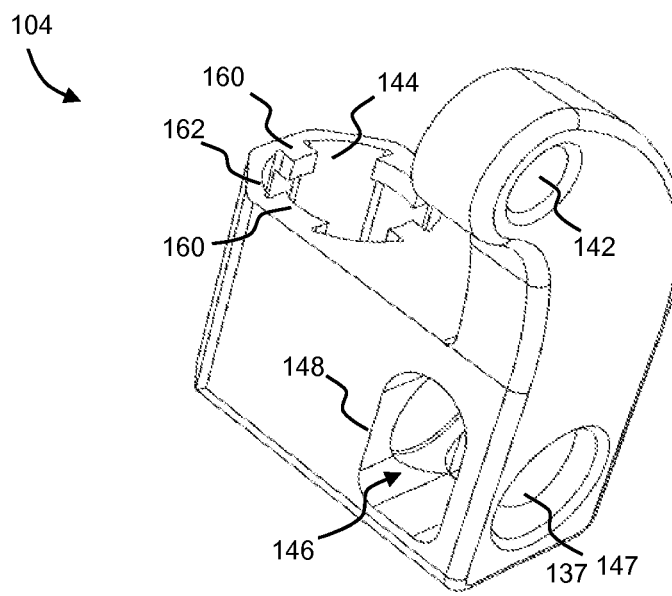

Referring now to FIG. 4, FIGS. 7A, and 7B, the second arm 104 includes an aperture 142 at the proximal end for receiving the linking member 108 and enabling the second arm 104 to pivot about the linking member 108. A front portion of the distal end includes a second SE receiver 144 for receiving a second one of the screw extenders 210 as shown in FIGS. 11A-12B. A rear portion of the distal end includes a second cavity 146 that receives the second pivot nut 124. The second cavity 146 may include a substantially cylindrical portion 147 that receives the second pivot nut 124. The cylindrical portion 147 may extend parallel to the linking member 108 and perpendicular to the coupler 110 of the assembled instrument 100. The second cavity 146 may communicate with an inner opening 148 on an inner surface of the distal end and an outer opening 150 on an outer surface of the distal end to allow the coupler 110 to pass through and rotate through a predetermined angle.

Figure 8A:
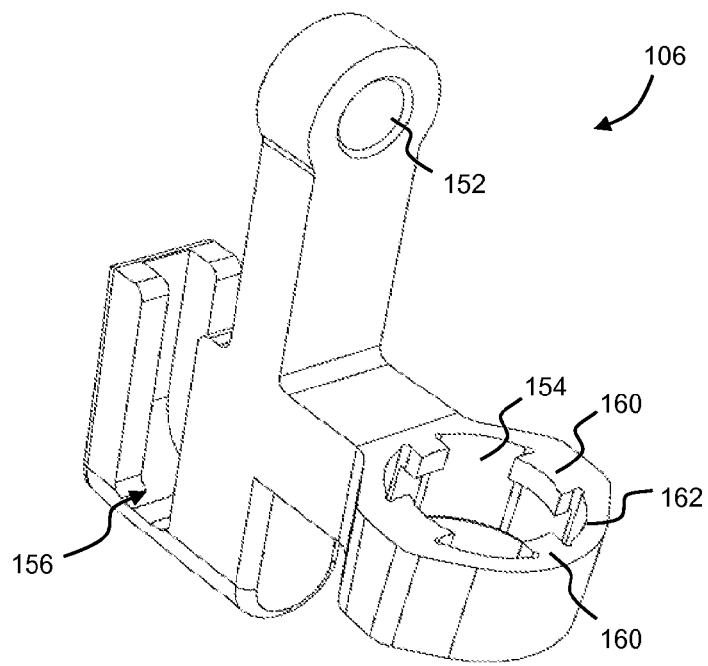
FIGS. 8A and 8B are front and rear perspective views of a third arm of the instrument according to the principles of the present disclosure.
Figure 8B:
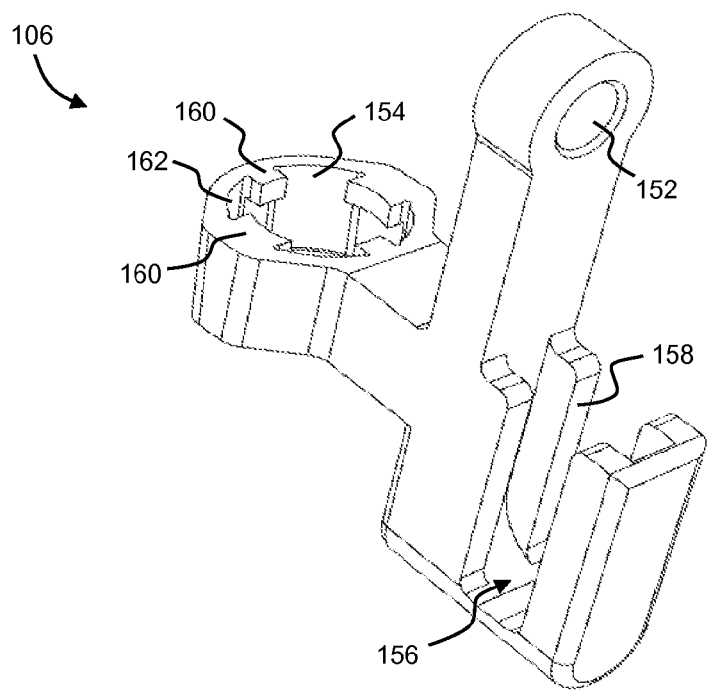
Figure 9A:
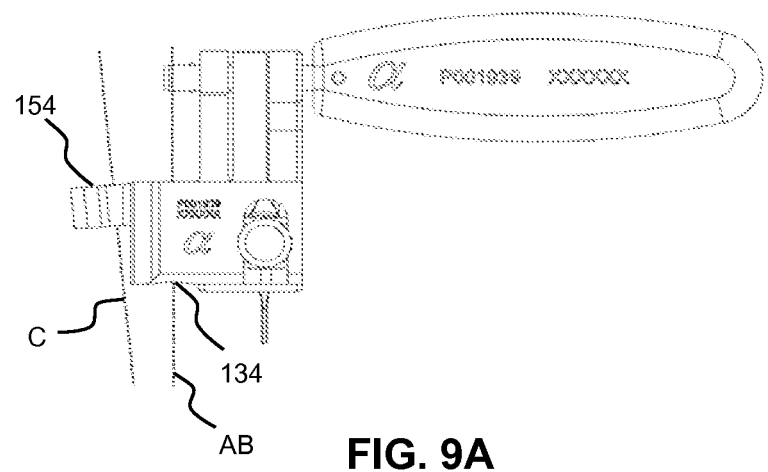
FIGS. 9A and 9B are side elevational views of the instrument and screw extenders according to the principles of the present disclosure.
Figure 9B:
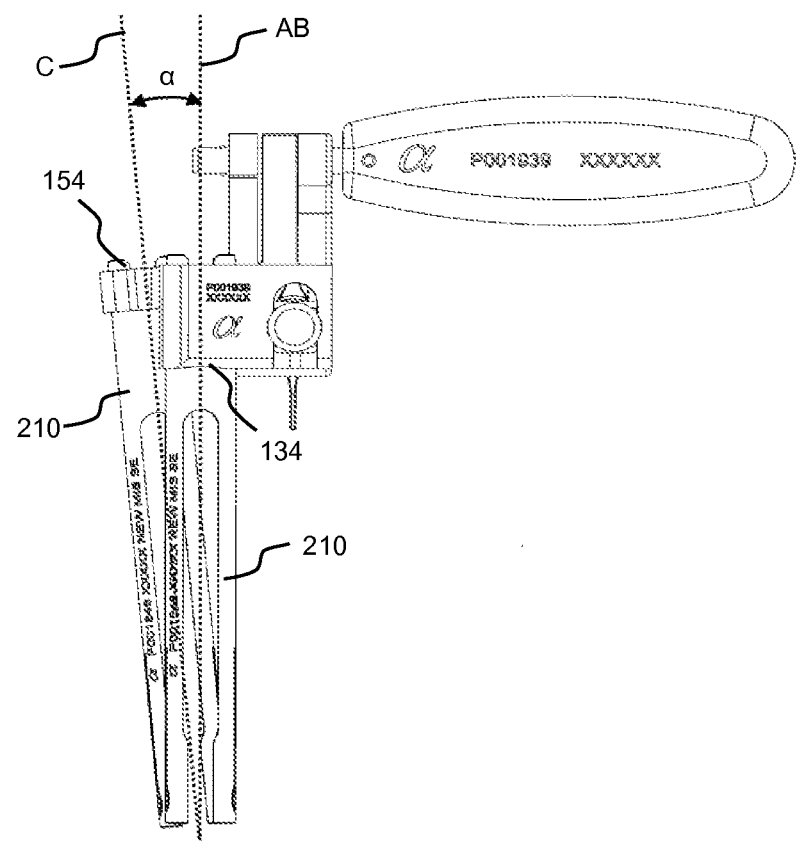

Referring now to FIGS. 4, 8A, and 8B, the third arm 106 includes an aperture 152 at the proximal end for receiving the linking member 108 and enabling the third arm 106 to pivot about the linking member 108. A front portion of the distal end includes a third SE receiver 154 for receiving a third one of the screw extenders 210 as shown in FIGS. 11A-12B. The third SE receiver 154 may be slightly angled relative to the first and second SE receivers 134 and 144 as illustrated in FIG. 11A-12B. For example, as illustrated by FIGS. 9A and 9B, a longitudinal axis C of the third SE receiver 154 may intersect a plane AB formed by a longitudinal axis A of the first SE receiver 134 and a longitudinal axis B of the second SE receiver 144. The intersection of axis C with the plane AB may form an angle α to facilitate alignment of the instrument 100 at the surgical site. In some examples, a hinge or flexible connection between the SE receiver 154 and arm 106 may provide a variable angle. A rear portion of the distal end includes a retention portion 156 for receiving the retaining portion 116 of the coupler 110. For example, the retention portion 156 may include a slotted portion 158 that receives the retention wheel 118. The retention wheel 118 may rotate freely within the slotted portion 158 and slide proximally and distally within the slotted portion 158 as the first arm 102 and second arm 104 move.

Each of the SE receivers 134, 144, and 154 may include various tabs 160, recesses 162, and/or other mating attachment features to enable secure attachment of the screw extenders 210 of the screw extender system 200. For example, as shown in FIGS. 6A-8B, each of the SE receivers 134, 144, and 154 includes tabs 160 that extend radially inwards. The tabs 160 form recesses 162 between one another. The recesses 162 may receive mating features on the proximal ends of the screw extenders 210 as described below. The tabs 160 may prevent rotation of the screw extenders 210 within the SE receivers 134, 144, and 154.

Referring back to FIG. 4, the instrument 100 may be assembled by inserting the coupler 110 into the third arm 106. The retention wheel 118 slides into the slot 158. The first pivot nut 122 may be inserted into the first cavity 136 and the second pivot nut 124 may be inserted into the second cavity 146. The first and second threaded portions 112 and 114 of the coupler 110 may be inserted through the inner openings 138 and 148 of the first and second arms 102 and 104 respectively. Each threaded portion may be threaded into the first and second pivot nuts 122 and 124 until the coupler 110 extends through the outer openings 140 and 150 of the first and second arms 102 and 104 respectively. The linking member 108 may be inserted through the apertures 132, 142, and 152 at the proximal ends of each of the arms 102, 104, and 106 respectively. The actuator 120, cap 126, and handle 130 may then be attached and secured with the pins 128.

Figure 10A:
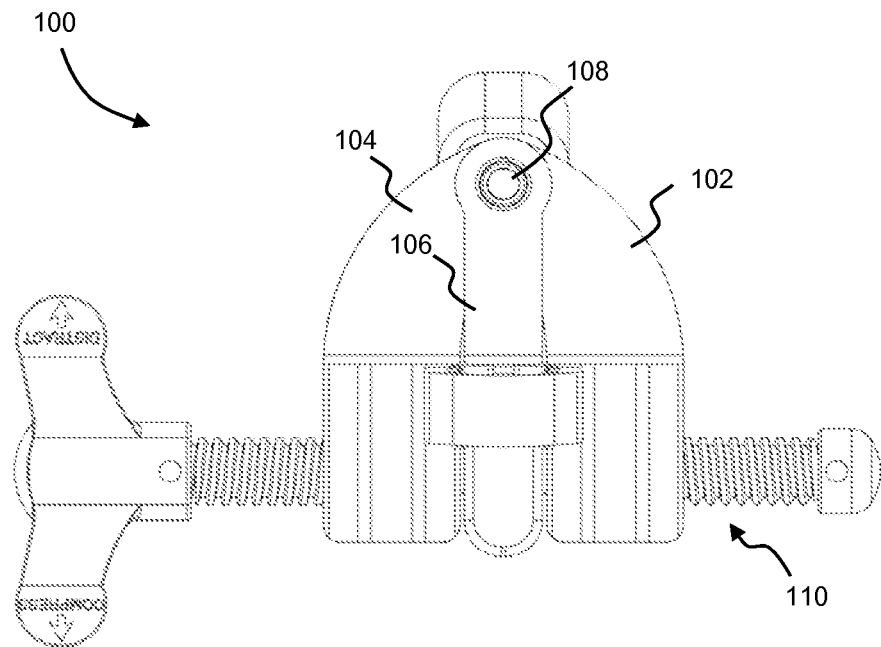
FIGS. 10A and 10B are front elevational views of the instrument according to the principles of the present disclosure.
Figure 10B:
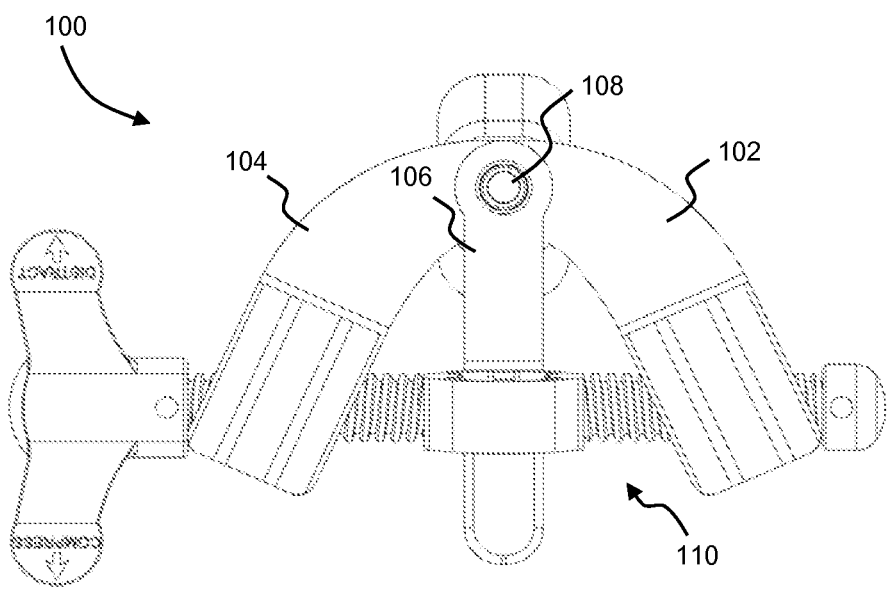
Figure 11A:
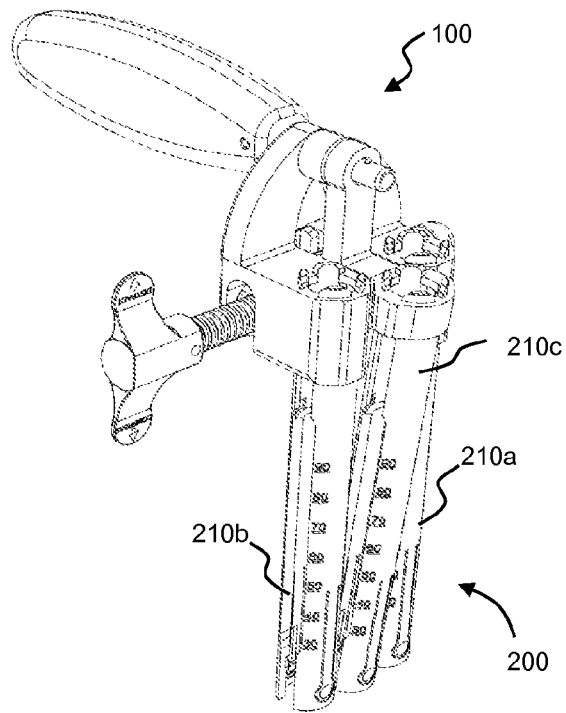
FIGS. 11A and 11B are font perspective views of the instrument and associated screw extenders according to the principles of the present disclosure.
Figure 11B:
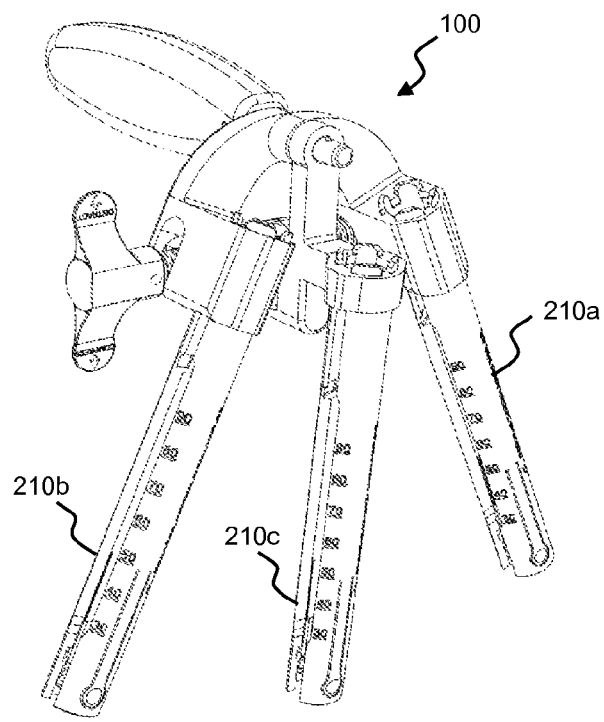

The instrument 100 may include a fully compressed position and fully distracted position as illustrated in FIGS. 10A and 10B respectively. The instrument 100 includes infinitely variable positioning between the fully compressed and fully distracted positions. Thus, gradual increases and decreases in the level of corrective force may be applied with gradual rotation of the coupler 110. Similar to a worm gear, the threaded engagement of the coupler 110 may also retain the position of the first arm 102 and second arm 104 while continuously applying corrective forces on the screw extenders 210 in FIG. 12B. For example, as the surgeon adjusts the instrument 100 from a first position to a second position, the threaded engagement constantly provides a locking or retaining force to prevent sudden collapse or expansion of the first and second arms 102 and 104 while applying corrective forces.

Referring now to FIGS. 11A-12B, the instrument 100 may apply a compressive or a distractive force on proximal ends of first, second, and third screw extenders 210a, 210b, and 210c (collectively screw extenders 210) that transfer the force to vertebrae V of the spinal column 300. The screw extenders 210 include distal ends that may attach to the vertebrae V via pedicle screws (now shown) or other attachment devices as known in the art and described herein. In the fully compressed position shown in FIG. 10A, the distal ends of a first screw extender 210a, a second screw extender 210b, and a third screw extender 210c may be tightly aligned. As the coupler 110 rotates, the first arm 102 and second arm 104 begin to move away from the third arm 106 causing the first and second screw extenders 210a and 210b to begin to fan away from the third screw extender 210c as shown in FIG. 11B.

In FIG. 12A, the first screw extender 210a is attached to a first vertebra V1, the second screw extender 210b is attached to a second vertebra V2, and the third screw extender 210c is attached to a third vertebra V3 located between the first and second vertebrae V1 and V2. Typically, insertion of the screw extenders 210 may be performed using minimally invasive surgical techniques. The third vertebra V3 may include trauma or a tumor that prevent a surgeon from maneuvering the vertebra. In FIG. 12B, the instrument 100 may be attached to the proximal ends of the screw extenders 210 to compress and distract the first and second vertebra V1 and V2 relative to the third vertebra V3. Each screw extender 210 may include mating features such as SE tabs 290 extending proximally away from the proximal ends. The SE tabs 290 interact with recesses 162 formed in the SE receivers 134, 144, and 154 on the instrument 100. The tabs 290 mate with the recesses 162 and the tabs 160 to prevent rotation of the screw extenders 210 within the SE receivers 134, 144, and 154 during compression and distraction procedures.

Figure 13A:
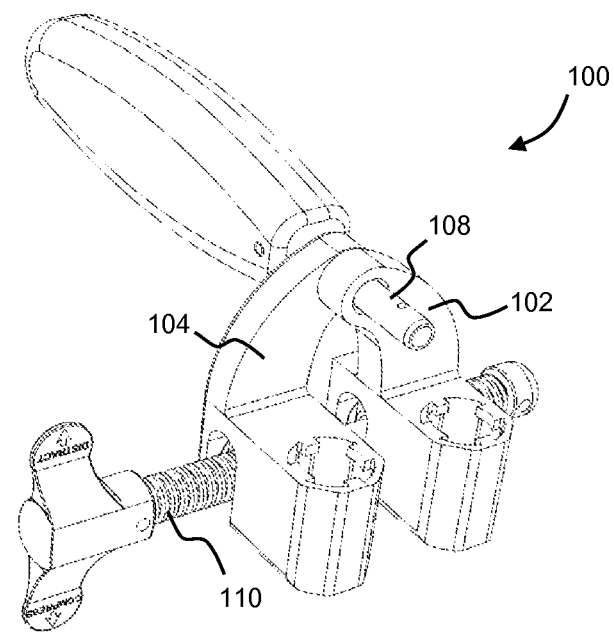
FIGS. 13A and 13B are front perspective views of the instrument in a configuration for single level compression and distraction according to the principles of the present disclosure.
Figure 13B:
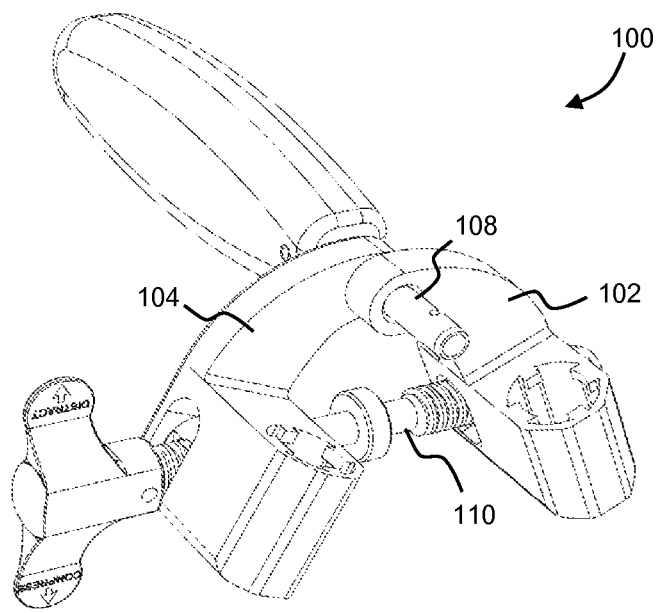

In some instances, compression and distraction procedures may not require skipping a vertebra. Referring now to FIGS. 13A and 13B, the instrument 100 may further be configured for single level compression and distraction procedures by removing the third arm 106. For example, one of the pins 128 may be removed to permit the third arm 106 to slide off of the linking member 108. The pin 128 may be reinserted into the linking member 108 to retain the first arm 102 and second arm 104.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An instrument for compression and distraction of vertebrae in a spinal column, comprising:
   a first arm including a distal end that receives a first screw extender that attaches to a first vertebra;
   a second arm including a distal end that receives a second screw extender that attaches to a second vertebra;
   a third arm including a distal end that receives a third screw extender that attaches to a third vertebra;
   a linking member that pivotally links proximal ends of the first, second, and third arms; and
   an actuator that positions the distal ends of the first arm and the second arm relative to the third arm to compress and distract the first vertebra and the second vertebra relative to the third vertebra,
   wherein rotating the actuator in a first direction positions the first arm and the second arm away from the third arm and rotating the actuator in a second direction positions the first arm and the second arm towards the third arm.

2. The instrument of claim 1, wherein the first arm and the second arm are disposed on opposite sides of the third arm.

3. The instrument of claim 1, further comprising a slot in the distal end of the third arm for receiving a wheel on the actuator.

4. The instrument of claim 1, further comprising cavities in the distal ends of the first arm and the second arm for receiving the actuator.

5. The instrument of claim 4, further comprising pivot nuts that pivot within the cavities and engage threads of the actuator to pivotally link the actuator with the first arm and the second arm.

6. The instrument of claim 1, wherein the first and second arms include first and second receivers for receiving the first and second screw extenders and having first and second longitudinal axes in a common plane.

7. The instrument of claim 6, wherein the third arm includes a third receiver for receiving the third screw extender and having a third longitudinal axis that intersects the common plane.

8. The instrument of claim 7, wherein each of the first, second, and third receivers includes one or more attachment features for attachment to the screw extenders.

9. The instrument of claim 7, wherein each of the first, second, and third receivers includes at least one of a tab and a recess for alignment and attachment to the screw extenders.

10. An instrument for multilevel compression and distraction of vertebrae of a spine, comprising:
 a first arm including a proximal end with an aperture and a distal end with a first screw extender receiver and a first pivot nut within the first arm;
 a second arm including a proximal end with an aperture and a distal end with a second screw extender receiver and a second pivot nut within the second arm;
 a third arm between the first and second arms and including a proximal end with an aperture and a distal end with a third screw extender receiver and a slotted portion within the third arm;
 a linking member extending through the apertures to pivotally connect the first, second, and third arms; and
 a threaded shaft extending through the distal ends and including a first threaded portion that engages the first pivot nut, a second threaded portion that engages the second pivot nut, and a retention wheel that rotates and slides within the slotted portion.

11. The instrument of claim 10, wherein the screw extender receivers include one or more attachment features to attach to screw extenders and prevent rotation of the screw extenders within the screw extender receivers.

12. The instrument of claim 10, wherein each of the pivot nuts includes a substantially cylindrical shape and an interior thread for engagement with the threaded portions of the threaded shaft.

13. The instrument of claim 10, wherein the distal ends of the first and second arms each include a cavity having a substantially cylindrical portion configured to receive the pivot nuts.

14. The instrument of claim 13, wherein the cylindrical portion extends parallel to the linking member and perpendicular to the threaded coupler.

15. The instrument of claim 13, wherein each cavity includes an inner opening on an inner surface of the distal end and an outer opening on an outer surface of the distal end to allow the threaded shaft to pass through and pivot.

16. The instrument of claim 10, wherein the third arm is removable.

17. The instrument of claim 10, wherein the first and second threaded portions are oppositely configured.

18. The instrument of claim 10, wherein the threaded shaft rotates causing the first arm and the second arm to pivot relative to the third arm.

* * * * *